United States Patent
Dann et al.

[11] Patent Number: 5,899,932
[45] Date of Patent: May 4, 1999

[54] METHOD OF AXIAL PREFERENTIAL THERMAL THERAPY

[75] Inventors: Mitchell Dann, Jackson, Wyo.; Jonathan R. McGrath, Chanhassen; Eric N. Rudie, Maple Grove, both of Minn.

[73] Assignee: Urologix, Inc., Minneapolis, Minn.

[21] Appl. No.: 08/824,064

[22] Filed: Mar. 24, 1997

Related U.S. Application Data

[62] Division of application No. 08/646,746, May 3, 1996, abandoned.

[51] Int. Cl.$^6$ .................................................. A61F 7/12
[52] U.S. Cl. ......................... 607/113; 607/96; 607/101; 606/28
[58] Field of Search ........................ 607/96, 100–105, 607/113, 116, 154, 156; 606/28, 29, 33, 41

[56] References Cited

U.S. PATENT DOCUMENTS

| | | | |
|---|---|---|---|
| 4,658,836 | 4/1987 | Turner | 128/804 |
| 4,841,988 | 6/1989 | Fetter et al. | 128/804 |
| 5,220,927 | 6/1993 | Astrahan et al. | 128/785 |
| 5,300,099 | 4/1994 | Rudie | 607/101 |
| 5,334,181 | 8/1994 | Rubinsky et al. | 606/22 |
| 5,417,689 | 5/1995 | Fine | 606/41 |
| 5,423,811 | 6/1995 | Imran et al. | 606/41 |
| 5,470,350 | 11/1995 | Buchholtz et al. | 607/97 |
| 5,472,405 | 12/1995 | Buchholtz et al. | 601/2 |
| 5,484,400 | 1/1996 | Edwards et al. | 604/22 |
| 5,492,529 | 2/1996 | Neuwirth et al. | 604/49 |
| 5,496,271 | 3/1996 | Burton et al. | 604/54 |
| 5,509,929 | 4/1996 | Hascoet et al. | 607/101 |
| 5,520,684 | 5/1996 | Imran | 606/41 |
| 5,733,315 | 3/1998 | Burdette et al. | 607/97 |

FOREIGN PATENT DOCUMENTS

| | | |
|---|---|---|
| 0 611 314 B1 | 12/1995 | European Pat. Off. . |
| WO 89/02292 | 3/1989 | WIPO . |
| WO 95/33514 | 12/1995 | WIPO . |
| WO 96/00036 | 1/1996 | WIPO . |

OTHER PUBLICATIONS

*Taylor & Francis International Journal of Hyperthermia*, "Cooled Microwave Transrectal Applicator with Adjustable Directional Beam for Prostate Treatment", vol. 11, No. 1, Jan.–Feb. 1995, pp. 95–108.

*Taylor & Francis International Journal of Hyperthermia*, "Design of Intracavitary Microwave Applicators for the Treatment of Uterine Cervix Carcinoma", vol. 7, No. 5, 1991, pp. 693–701.

*Taylor & Francis International Journal of Hyperthermia*, "Application of New Technology in Clinical Hyperthermia ", vol. 10, No. 3, 1994, pp. 389–394.

*Primary Examiner*—Max Hindenburg
*Assistant Examiner*—Bryan K. Yarnell
*Attorney, Agent, or Firm*—Kinney & Lange, P.A.

[57] ABSTRACT

A method of prostate treatment includes the step of inserting into a prostatic portion of urethra an energy emitting device that is connected to an energy source. Energy is delivered to the prostate from the energy emitting device. The amount of energy emitted to prostatic tissue adjacent to a bladder is greater than that emitted to prostatic tissue distant from the bladder.

4 Claims, 9 Drawing Sheets

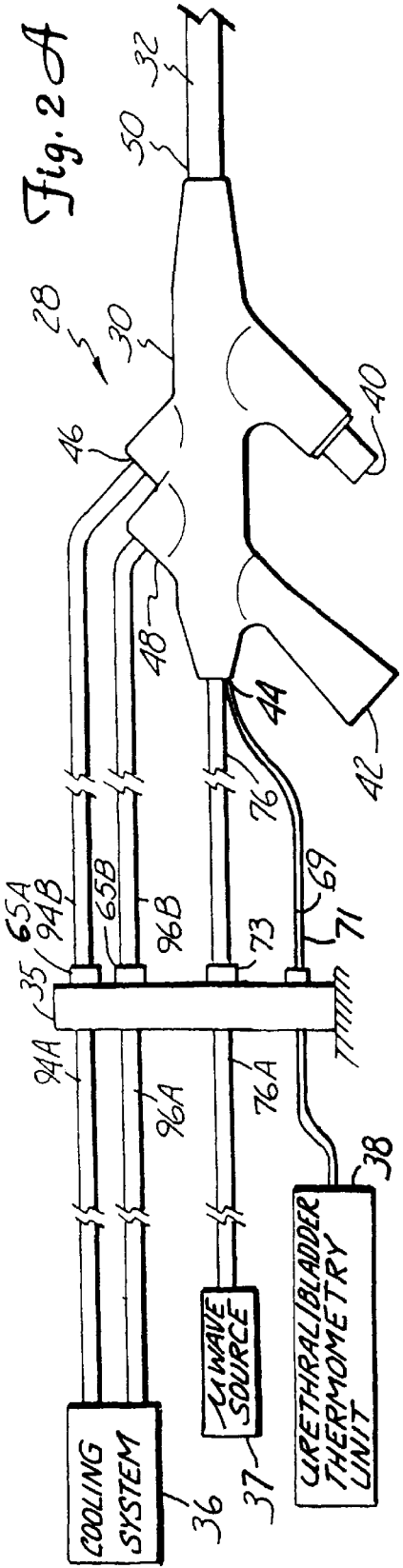
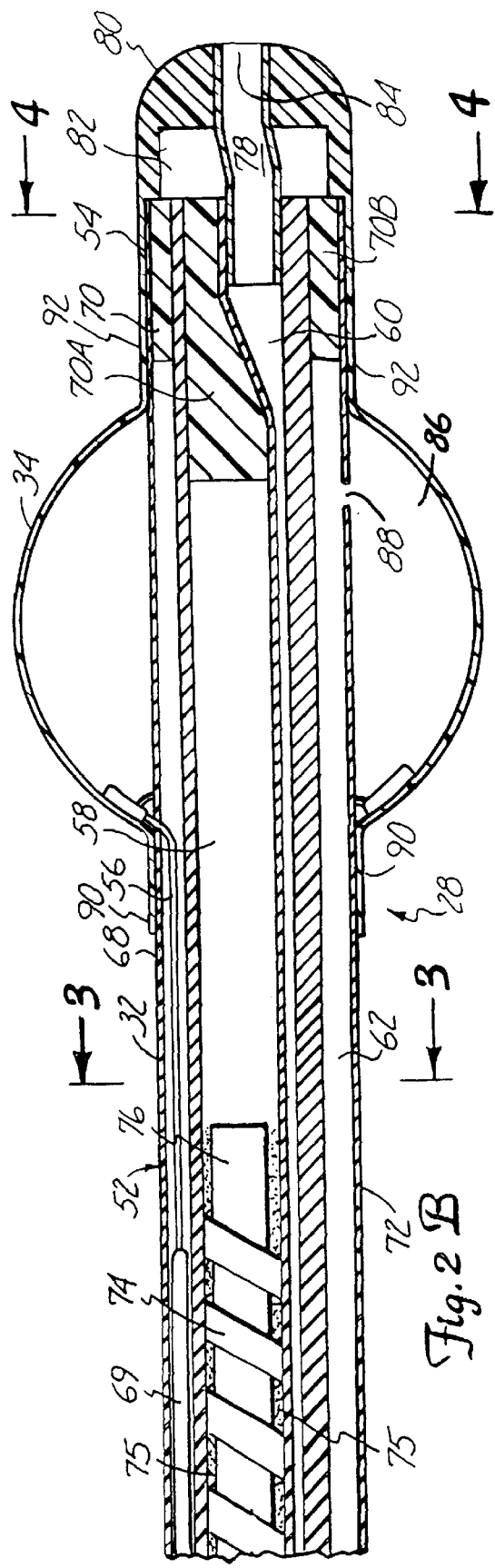

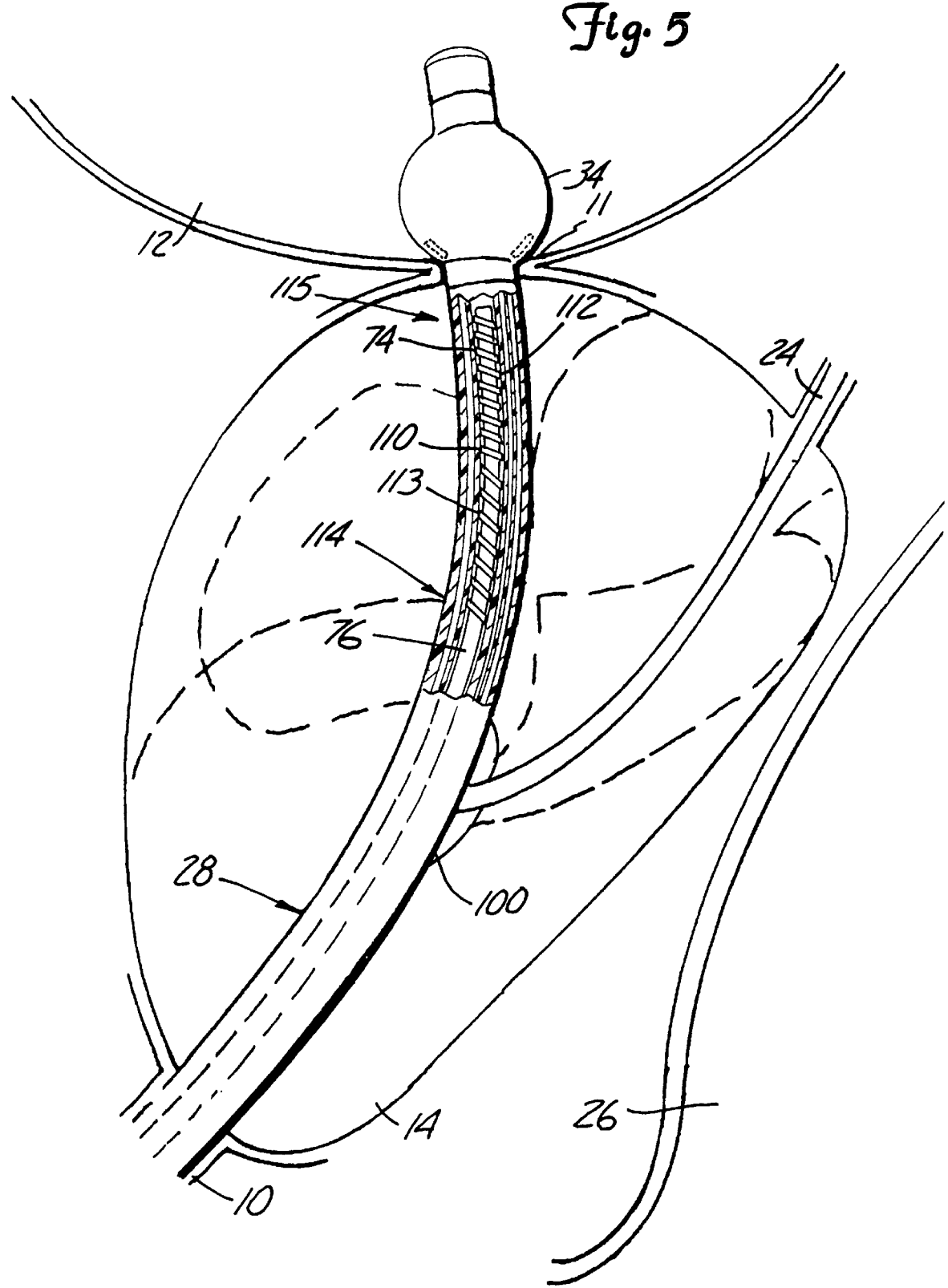

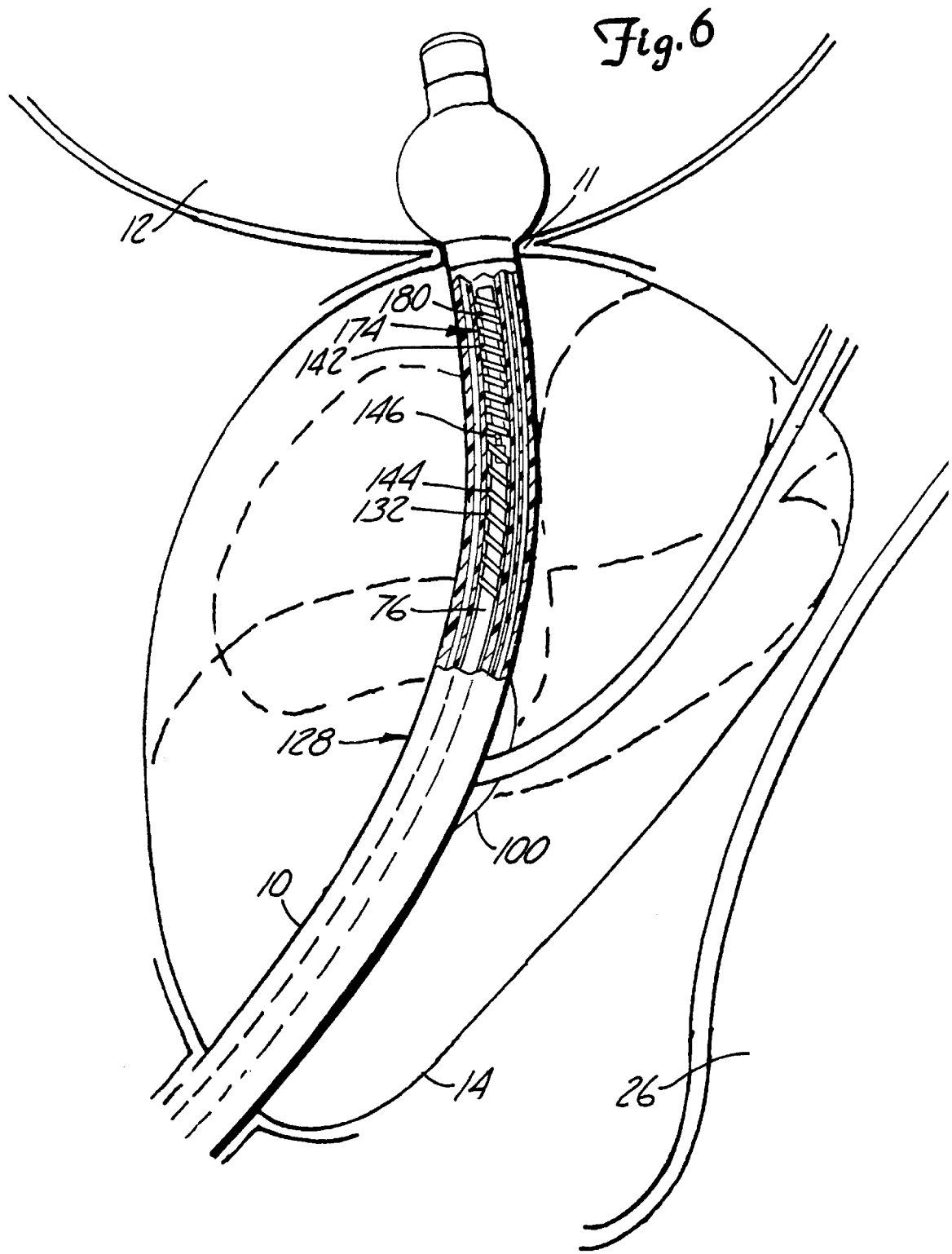

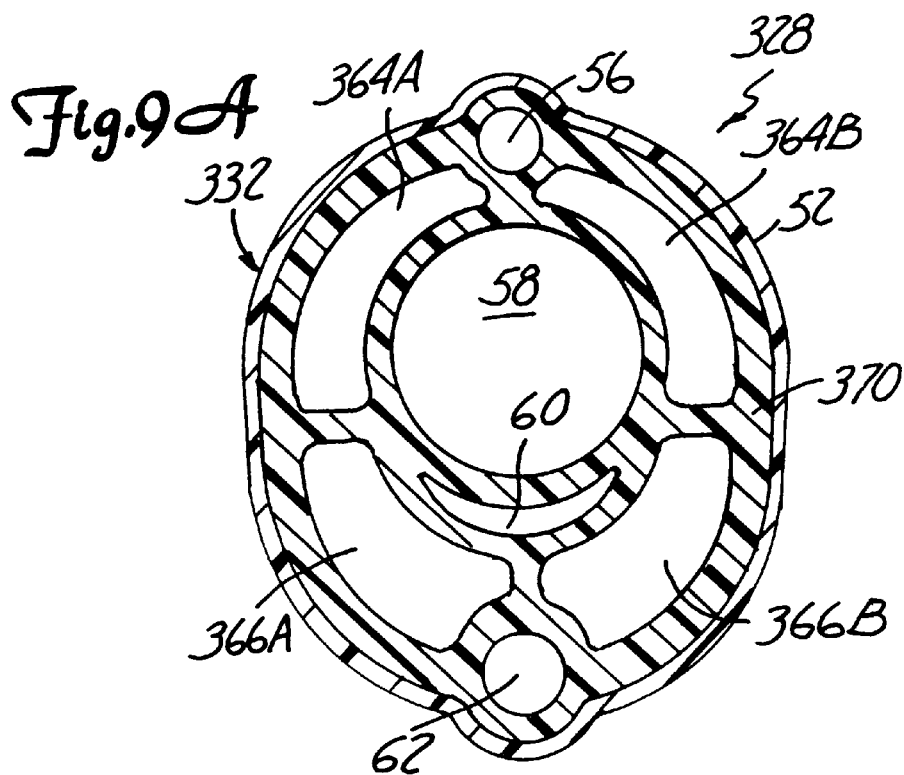
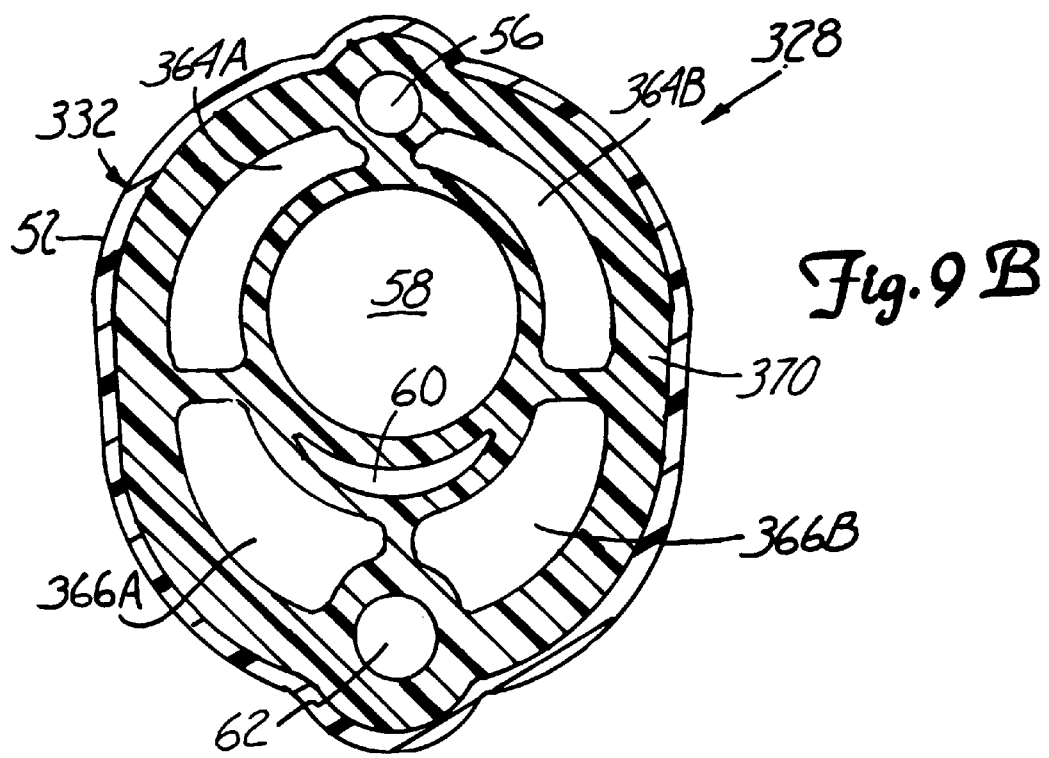

METHOD OF AXIAL PREFERENTIAL THERMAL THERAPY

CROSS-REFERENCE TO RELATED APPLICATIONS

This is a division of application Ser. No. 08/646,746, filed May 3, 1996, now abandoned.

BACKGROUND OF THE INVENTION

The present invention relates to methods for treating the prostate. In particular, the present invention relates to a method of delivering varying amounts of energy to the prostate along the prostatic urethra.

The prostate gland is a complex, chestnut-shaped organ which encircles the urethra immediately below the bladder. The portion of the urethra extending through the prostate (i.e., the prostatic urethra) includes a proximal segment, which communicates with the bladder, and a distal segment, which extends at an angle relative to the proximal segment by the verumontanum.

Although a relatively small organ, the prostate is the most frequently diseased of all internal organs and is often the site of a common affliction among older men, benign prostatic hyperplasia (BPH), as well as a more serious affliction, cancer. BPH is a nonmalignant, bilateral expansion of prostate tissue occurring mainly in the transition zone of the prostate adjacent to the proximal segment of the prostatic urethra. As this tissue grows in volume, it encroaches on the urethra extending into the region of the bladder neck at the base of the bladder. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

Benign prostatic hyperplasia (BPH) may be treated using transurethral thermal therapy as described in further detail in U.S. Pat. 5,413,588 entitled DEVICE FOR ASYMMETRICAL THERMAL THERAPY WITH HELICAL DIPOLE MICROWAVE ANTENNA and in co-pending U.S. patent application Ser. No. 08/309,137 entitled COOLANT PRE-CHILLING PRIOR TO BENIGN PROSTATIC HYPERPLASIA TREATMENT, both of which are herein incorporated by reference. During transurethral thermal therapy, the transition zone of the prostate is heated to necrose the tumorous tissue that encroaches on the urethra. Transurethral thermal therapy is administered by use of a microwave antenna-containing catheter which includes a multi-lumen shaft. The catheter is positioned in the urethra with the microwave antenna located adjacent to the hyperplastic prostatic tissue. Energization of the microwave antenna causes the antenna to emit electromagnetic energy which heats tissue within the prostate.

One of the main objectives of transurethral thermal therapy is to selectively deliver a sufficient intensity of electromagnetic energy to the hyperplastic tissues of the prostate to generate necrosis-producing temperatures in those tissues without harming adjacent healthy tissue. In this regard, it is important to avoid thermal damage to urethral, rectal and bladder neck tissues.

Damage to the bladder neck may cause such complications as bladder contractures and trigone damage. Bladder neck contractures occur when the muscle of the bladder neck becomes damaged and as a result contracts and becomes fibrotic. As a result, the opening between the bladder neck and the urethra narrows and possibly closes due to scarring. Occlusion of the opening between the bladder neck and the urethra causes urinary retention. However, removal of scarring to reopen the opening between the bladder neck and the urethra poses a risk of severe infections and bladder stones. In addition, removing scarring often leads to additional new scarring. As a result, bladder neck contractures require continual treatment.

Damage to the bladder wall or trigone occurs when the portion of the bladder wall located between the urethral orifices and the bladder neck is damaged by excessive heat such as that caused by electromagnetic energy. The trigone contains nerves which signal the need for urination. As a result, damage to the trigone causes irritation, dysuria, which is pain upon urination, and possibly hematuria bleeding.

SUMMARY OF THE INVENTION

The present invention is a method for treating prostate conditions, such as benign prostatic hyperplasia (BPH). The method includes the step of delivering energy to the prostate to elevate a temperature of prostatic tissue sufficient to cause necrosis of the prostatic tissue. The amount of energy delivered to the prostatic tissue varies longitudinally along the prostatic urethra.

In one preferred embodiment, a first amount of electromagnetic energy is delivered to prostatic tissue adjacent to the bladder and a second amount of electromagnetic energy, less than the first amount, is delivered to prostatic tissue distant from the bladder.

BRIEF DESCRIPTION OF THE DRAWINGS

FIG. 2A is a side view of the distal end of a urethral catheter of the present invention.

FIG. 2B is an enlarged sectional view of the proximal end of the urethral catheter of the present invention.

FIG. 5 is an enlarged vertical sectional view of the proximal end of the urethral catheter of the present invention positioned within the prostate region.

FIG. 6 is an enlarged vertical sectional view of a first alternative embodiment of the catheter of the present invention positioned within the prostate region.

FIG. 9A is a cross-sectional view of a third alternate embodiment of the urethral catheter of the present invention.

FIG. 9B is a cross-sectional view of the urethral catheter of FIG. 9A.

DETAILED DESCRIPTION OF THE PREFERRED EMBODIMENTS

Figure 1:
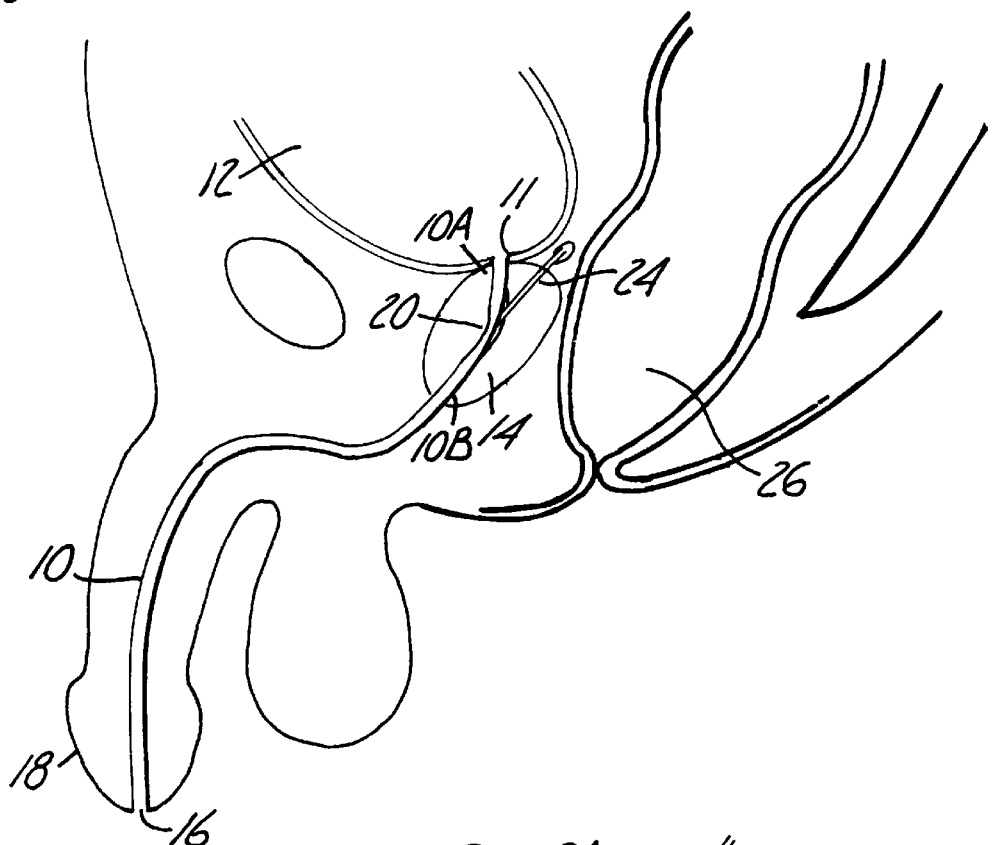
FIG. 1 is a vertical sectional view of a male pelvic region showing the urinary organs effected by benign prostatic hyperplasia.

FIG. 1 is a vertical sectional view of a male pelvic region showing the effect benign prostatic hyperplasia (BPH) has on the urinary organs. Urethra 10 is a duct leading from bladder neck 11 of bladder 12, through prostate 14 and out orifice 16 of penis end 18. Urethra 10 comprises proximal urethral segment 10A, which communicates with bladder 12 at bladder neck 11, and distal urethral segment 10. Benign tumorous tissue growth within prostate 14 tends to be located adjacent to proximal urethral segment 10A from bladder neck 11 to the junction of the proximal and distal urethral segments, which causes constriction 20 of urethra 10 and interrupts the flow of urine from bladder 12 to orifice 16. The tumorous tissue of prostate 14 which encroaches urethra 10 and causes constriction 20 can be effectively removed by heating and necrosing the encroaching tumorous tissue. Ideally, with the present invention, only periurethral tumorous tissue of prostate 14 anterior and lateral to urethra 10 is heated and necrosed to avoid unnecessary and undesirous damage to urethra 10 and to adjacent healthy tissues, such as bladder 12, bladder neck 11, ejaculatory duct 24 and rectum 26. A selective heating of prostate 14 (transurethral thermal therapy) is made possible by microwave antenna-containing catheter 28 of the present invention, which is shown in FIGS. 2A, 2B, 3, 4 and 5.

FIG. 2A shows a side view of a distal end of catheter 28. FIG. 2B shows an enlarged sectional view of a proximal end of catheter 28. As shown in FIGS. 2A and 2B, catheter 28 generally includes multi-port manifold 30, multi-lumen shaft 32, shaft position retention balloon 34, connection manifold 35, cooling system 36, microwave generating source 37 and urethral/bladder thermometry unit 38.

Multi-port manifold 30 includes inflation port 40, urine drainage port 42, microwave antenna port 44, cooling fluid in port 46 and cooling fluid out port 48. Ports 40–48 communicate with corresponding lumens within shaft 32. Manifold 30 is preferably made of medical-grade silicone sold by Dow Corning under the trademark Silastic Q-7-4850.

Figure 3:
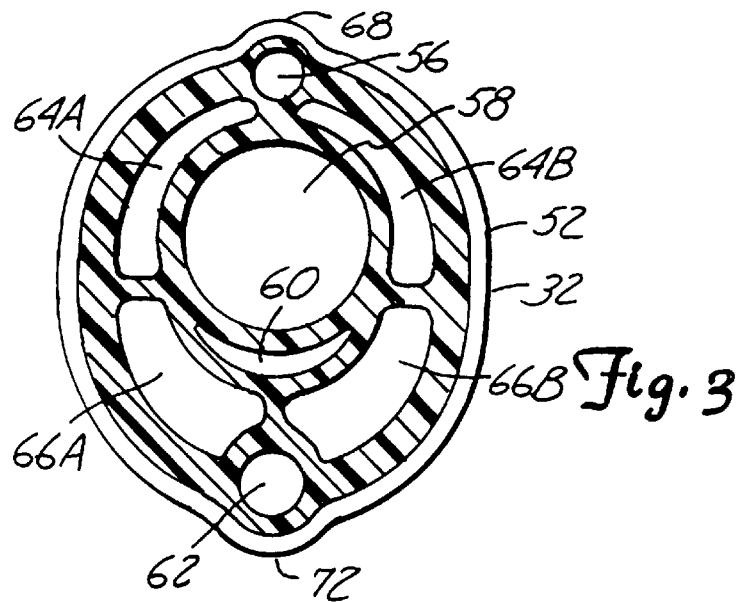
FIG. 3 is a cross-sectional view of the urethral catheter of FIG. 2B taken along line 3—3.

Multi-lumen shaft 32 is connected to manifold 30 at shaft distal end 50. Shaft 32 is a multi-lumen, Foley-type urethral catheter shaft which is extruded from a flexible, medical-grade silicone sold by Dow Corning under the trademark Silastic Q-7-4850. Shaft 32, which has an outer diameter of about 19 French, includes outer surface 52, which is generally elliptical in cross-section as shown in FIG. 3. Shaft 32 is long enough to permit insertion of proximal shaft end 54 through urethra 10 and into bladder 12. In one preferred embodiment, shaft 32 is coated with a hydrophilic solution sold by Hydromer, Inc. under the mark Hydromer, which lubricates outer surface 52 of shaft 32 and facilitates its advancement within urethra 10.

As shown in FIGS. 2B-4, shaft 32 includes temperature sensing lumen 56, microwave antenna lumen 58, urine drainage lumen 60, balloon inflation lumen 62, cooling fluid intake lumens 64A and 64B, and cooling fluid exhaust lumens 66A and 66B. Lumens 56–66B generally extend from distal shaft end 50 to proximal shaft end 54.

As shown in FIG. 2B, temperature sensing lumen 56 is positioned near first side 68 of shaft 32. Temperature sensing lumen 56 communicates with microwave antenna port 44 and receives a multi-fiber thermosensor which constitutes urethral thermometry sensor 69 and bladder thermometry sensors 71. Urethral thermometry sensor 69 is positioned within shaft 32 so as to be situated adjacent to prostate 14 when shaft 32 is inserted within urethra 10 to monitor the temperature of surrounding tissue. Sensor 69 exits through port 44 and is connected through connection manifold 35 to urethral thermometry unit 38. Urethral thermometry unit 38 measures urethral temperature based upon signals from temperature sensor 69 within catheter 28.

Bladder thermometry sensors 71 are positioned at a distal portion of balloon 34 adjacent to the wall of balloon 34 so as to be situated by the bladder neck when balloon 34 is inflated and fixed in the bladder. Bladder thermometry sensor 71 preferably includes three temperature sensors 71A, 71B, 71C, which are generally equidistantly spaced from one another. Sensors 71 exit through port 44 and are also connected through connection manifold 35 to urethral/ bladder thermometry unit 38, to measure bladder neck temperature based upon signals from temperature sensors 71. Bladder thermometry sensors 71A–71C and urethral/ bladder thermometry unit 38 measure bladder neck temperature and the temperature of prostate 14 adjacent bladder neck 11. By monitoring bladder neck temperature, the amount of electromagnetic energy emitted by antenna 74 to prostate tissue proximate to bladder neck 11 (shown in FIG. 1) can be controlled to avoid damage to bladder neck 11. In a preferred embodiment, thermometry sensors 69 and 71 A–71C are fiber optic luminescence type temperature sensors sold by Luxtron Corporation. Temperature sensing lumen 56 is sealed at proximal end 54 by silicone plug 70.

Figure 4:
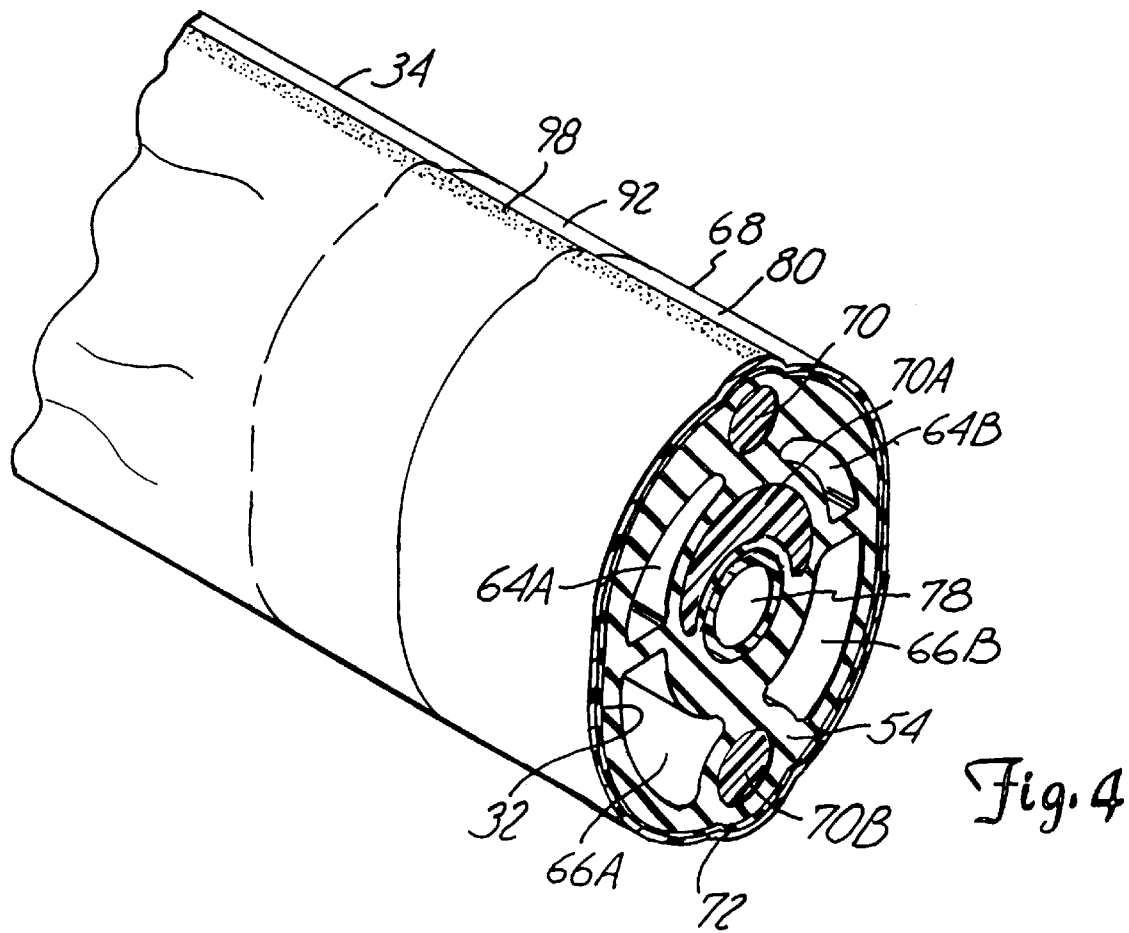
FIG. 4 is a perspective view of a proximal end of the urethral catheter with the end portion taken in section from line 4—4 of FIG. 2B.

As shown in FIGS. 3 and 4, microwave antenna lumen 58 is eccentric to the longitudinal axis of shaft 32, antenna lumen 58 being positioned nearer first side 68 of shaft 32 than second side 72 of shaft 32. Antenna lumen 58 is sealed at proximal end 54 by silicone plug 70A. At its distal end, antenna lumen 58 communicates with microwave antenna port 44. In one embodiment, microwave antenna 74 (shown in FIG. 2B) is permanently positioned within antenna lumen 58 near balloon 34. Antenna 74 is positioned within antenna lumen 58 so as to be generally situated in the proximal urethral segment 10A adjacent to the benign tumorous tissue of prostate 14 when shaft 32 is properly positioned within urethra 10. As shown in FIGS. 2A–2B, in one embodiment, antenna 74 is bonded within antenna lumen 58 by adhesive bond 75. Antenna 74 is carried at the proximal-most end of coaxial cable 76. The distal-most end of coaxial cable 76 is connected to connection manifold 35 by a conventional quick-coupling fitting 73. Coaxial cable 76 communicates with microwave generating source 37 by connection cable 76A, which is connected between microwave generating source 37 and connection manifold 35. In one embodiment, connection cable 76A is a standard RG 400 coaxial cable. Microwave generating source 37 produces a maximum of 100 watts of electrical power at a frequency of about 915 MHz±13 MHz, which is within the FCC-ISM standards. When antenna 74 is energized by microwave generating source 37, antenna 74 emits electromagnetic energy which causes heating of tissue within prostate 14.

Urine drainage lumen 60 is positioned adjacent antenna lumen 58, between antenna lumen 58 and second side 72. Urine drainage lumen 60 communicates with urine drainage port 42 and defines a drainage path for urine when proximal end 54 of shaft 32 is inserted within bladder 12. Urine drainage lumen 60 is connected to urine drainage lumen extension 78 at proximal end 54. Urine drainage lumen extension 78 is bonded within proximal end cap 80. End cap 80 is further bonded over outer surface 52 of shaft 32 at proximal shaft end 54, with cavity 82 surrounding lumen extension 78. With end cap 80 and urine drainage lumen extension 78 in place, opening 84 to lumen extension 78 permits urine to drain from bladder 12 through urine drainage lumen 60 and out urine drainage port 42 when proximal shaft end 54 is inserted within bladder 12. Drainage of urine from bladder 12 is necessary due to frequent bladder spasms which occur during transurethral thermal therapy.

Balloon inflation lumen 62 is positioned near second side 72, generally between urine drainage lumen 60 and second side 72. Balloon inflation lumen 62 communicates with inflation port 40 and is sealed at proximal end 54 by silicone plug 70B. Balloon inflation lumen 62 communicates with interior 86 of balloon 34 by opening 88.

Balloon 34, which is formed from a tubular section of a flexible, medical-grade silicone sold by Dow Corning under the trademark Silastic Q-7-4720, is secured over shaft 32 by bonding balloon waists 90 and 92 over exterior surface 52 of shaft 32 near proximal shaft end 54. Balloon 34 is inflated (e.g. by air) by an inflation device (not shown), which is connected to inflation port 40 and which supplies positive fluid pressure to interior 86 of balloon 34. Balloon 34 is deflated when the inflation device supplies a negative fluid pressure (i.e., a vacuum) to interior 86 of balloon 34. Balloon 34 serves to retain shaft 32 in a fixed position within urethra 10 when balloon 34 is inflated within bladder 12 near bladder neck 11, as shown in FIG. 5. When inflated, balloon 34 also preferably supports sensors 71A–71C adjacent to bladder neck 11.

As shown in FIG. 2B, FIG. 3 and FIG. 4, cooling fluid intake lumens 64A, 64B are positioned circumjacent to first side 68, between first side 68 and antenna lumen 58. Cooling fluid intake lumens 64A, 64B extend from distal shaft end 50 to proximal shaft end 54 where lumens 64A, 64B are exposed to cavity 82 of end cap 80. Intake lumens 64A, 64B are relatively narrow in cross-section and have a relatively small cross-sectional surface area. Water contained within intake lumens 64A, 64B performs two essential functions. First, water contained within lumens 64A, 64B absorbs some of the microwave energy emitted by antenna 74. This assists, in part, in controlling the volume of tissue adjacent to first side 68 of shaft 32 that is heated above about 45° C. Second, the water within lumens 64A, 64B absorbs heat energy generated by the microwave energy from adjacent tissues (i.e., urethra 10) via thermal conduction. This prevents urethra 10 from being overheated and damaged when antenna 74 is energized.

Cooling fluid exhaust lumens 66A, 66B are circumjacent to second side 72 with lumens 66A, 66B generally positioned between second side 72 and antenna lumen 58. Like intake lumens 64A, 64B, exhaust lumens 66A, 66B extend from shaft distal end 50 to shaft proximal end 54 where exhaust lumens 66A, 66B are exposed to cavity 82 of end cap 80. Exhaust lumens 66A, 66B are wider in cross-section than intake lumens 64A, 64B, and have a cross-sectional area greater than the cross-sectional area of intake lumens 64A, 64B. Water within exhaust lumens 66A, 66B is therefore capable of absorbing a greater amount of microwave energy when antenna 74 is energized. As a result, for a given power output from microwave generating source 37, a relatively large volume of tissue adjacent second side 72 will remain below about 45° C. Water within exhaust lumens 66A, 66B also absorbs heat energy from adjacent tissue (i.e., urethra 10) when antenna 74 is energized, which prevents the urethra from being overheated and damaged when antenna 74 is energized.

Intake lumens 64A, 64B and exhaust lumens 66A, 66B are supplied with water from cooling system 36. Water from cooling system 36 is chilled and maintained at a temperature of between about 7° C. to 25° C., preferably at about 8° C., and pumped at a rate of between about 100–150 milliliters per minute via water feed line 94A to connection manifold 35. The water flows through connection manifold 35 to water feed line 94B and to water intake port 46, which communicates with water intake lumens 64A, 64B. Under fluid pressure, the water circulates through intake lumens 64A, 64B to cavity 82 of end cap 80. The water returns to cooling system 36 through exhaust lumens 66A, 66B to fluid exhaust port 48. The water is carried from water exhaust port 48 via water return line 96B to connection manifold 35, and from connection manifold 35 to cooling system 36 via water return line 96A. The water is then re-chilled and re-circulated. Water feed line 94B and water return line 96B are each provided with a conventional quick-coupling fitting 65A and 65B, respectively, which permits catheter 28 to be easily disconnected from cooling system 36.

FIG. 5 is an enlarged vertical sectional view of the proximal end of catheter 28 inserted into a prostatic portion of urethra 10. As shown by FIG. 5, proximal end of catheter 28 is inserted into urethra 10 so as to position balloon 34 within bladder 12 at bladder neck 11. Once positioned within bladder 12, balloon 34 is inflated as shown in FIG. 5 to anchor shaft 32 in a relatively fixed position within urethra 10.

As further shown by FIG. 5, microwave antenna 74 is carried at the proximal-most end of coaxial cable 76 and is generally situated between bladder neck 11 and verumontanum 100. Preferably, the proximal-most end 115 of antenna 74 is spaced from balloon 34 and is spaced from bladder neck 11 by a distance sufficient to produce necrosis of as much hyperplastic prostatic tissue as possible without damaging bladder neck 11. In one embodiment, antenna 74 is longitudinally spaced from balloon 34 by a distance of about 0.5 cm. The distal-most end 114 of antenna 74 is preferably positioned just proximal of verumontanum 100. Antenna 74 has a generally helical dipole construction as further described in U.S. Pat. No. 5,300,099, which is incorporated by reference herein. Antenna 74 is preferably formed from a single elongate wire section helically wound about cable 76 to form windings 110. Windings 110 are asymmetrically or unequally spaced from one another along an axial length of cable 76.

As best shown by FIG. 5, windings 110 of antenna 74 are preferably spaced closer to one another at the proximal-most end 115 of antenna 74 in the vicinity of bladder neck 11 than the distal-most end 114 of antenna 74 in the vicinity of verumontanum 100. In other words, antenna 74 has a smaller pitch in the vicinity of bladder 22 than in the vicinity of verumontanum 100. Preferably, a first portion 112 of the wire section forming antenna 74 has a first pitch and a second portion 113 of the wire section forming antenna 74 has a second pitch, which is larger than the first pitch of first portion 112. As a result, for a given amount of power delivered to antenna 74, portion 112 of antenna 74 emits a greater power per unit mass of electromagnetic energy, commonly known as specific absorption rate (SAR), to prostatic tissue proximate to bladder neck 11 than the SAR of electromagnetic energy directed at prostatic tissue adjacent verumontanum 100 by section 113 of antenna 74. Antenna 74 emits and directs electromagnetic energy along its axis to asymmetrically deliver energy to prostatic tissue along an axis of antenna 74 between bladder neck 11 and verumontanum 100. This asymmetrical delivery of energy along the axis of antenna 74 enables a sufficient elevation of the temperature of prostatic tissue along the axis of antenna 74 to achieve a desired volume of tissue necrosis about urethra 10.

In one embodiment, windings 110 are equally spaced from one another along the length of each portion 112, 113. Consequently, this configuration of antenna 74 produces a generally stepped deliverance of electromagnetic energy to prostatic tissue along an axis of antenna 74. In an alternative embodiment, the spacings between windings 110 or the pitch of antenna 74 may be gradually reduced from distal end 114 of antenna 74 towards proximal end 115 of antenna 74 to deliver a gradually varying distribution of electromagnetic energy to prostatic tissue.

The intensity or SAR of electromagnetic energy emitted is directly proportional to the heat produced in a medium within the electromagnetic field. Unless dissipated, the entire amount of heat produced in the medium results in a corresponding temperature elevation of the medium. In a homogenous medium, temperature elevation of the medium directly corresponds to the amount of heat produced in the medium. As a result, peak temperatures are achieved where the intensity of the electromagnetic energy is the greatest, absent any cooling between the antenna and the adjacent medium. For a longitudinally uniform radial distribution of electromagnetic energy, the temperature distribution for a given volume will be generally symmetrical, essentially reflecting the distribution of electromagnetic energy in that given volume.

Tissue, however, is not a homogenous medium. In tissue, vascularity impacts the tissue's ability to dissipate heat, with well vascularized tissue being able to dissipate heat better than less vascularized tissue. It has recently been discovered that improved treatment of BPH may be achieved by delivering a greater amount of energy, such as electromagnetic energy, to prostatic tissue in a vicinity of the bladder neck 11 than in a vicinity of the verumontanum 100. In particular, it has been discovered that tissue of prostate 14 proximate to bladder neck 11 may have an increased vascularity relative to portions of prostate 14 in the vicinity of verumontanum 100. Due to this increased vascularity, the tissue of prostate 14 proximate to bladder neck 11 has an increased ability to vent or carry away excess heat. As a result, for a given power level, a longitudinally uniform radial distribution of electromagnetic energy results in an asymmetrical temperature elevation of the prostate with less temperature rise adjacent to the bladder neck than is desirable to provide the most effective therapy possible. Because section 112 of antenna 74 directs a greater amount of electromagnetic energy to prostatic tissue in a vicinity of bladder neck 11 than section 113 of antenna 74 directs to prostatic tissue in a vicinity of verumontanum 100, catheter 28 is able to supply more heat energy to prostatic tissue in the vicinity of bladder neck 11 to overcome the newly discovered increased vascularity and energy venting ability of prostate tissue proximate to bladder neck 11. This enables sufficient temperature elevation to necrose a suitable volume of tissue near the bladder neck.

FIG. 6 is an enlarged vertical sectional view of catheter 128, a first alternative embodiment of the present invention, with the proximal end of catheter 128 inserted into a prostatic portion of urethra 10. Catheter 128 has all the attributes and features of catheter 28 shown in FIGS. 2–5 except that catheter 128 includes antenna 174 in lieu of antenna 74. For ease of illustration, those remaining elements of catheter 128 which are the same as corresponding elements of catheter 28 are similarly numbered. Antenna 174 is similar to antenna 74 except that instead of being formed from a single wire section, antenna 174 is formed from wire sections 142 and 144 which are interconnected by connector 146. Wire section 142 is formed from a single section of wire helically coiled or wrapped about cable 76 at proximal end 115 of cable 76 proximate to bladder neck 11. Wire section 142 includes windings 180 that are preferably equally spaced along an axis of cable 76.

Wire section 144 is formed from a single segment of wire helically wrapped or coiled about cable 76 at a distal end 114 of antenna 174 towards and in the vicinity of verumontanum 100. Wire section 144 includes a plurality of windings 182 which are equally spaced from one another along an axis of cable 76. The spacing between windings 182 of wire section 144 is greater than spacing between windings 180 of wire section 142. In other words, wire section 144 has a greater pitch than wire section 142. As a result, wire section 142 of cable 76 directs a greater amount of electromagnetic energy at prostatic tissue than does wire section 144. Thus, antenna 174 produces an electromagnetic energy distribution profile such that the temperature distribution in the prostatic tissue in the vicinity of bladder neck 11 approximates the temperature distribution in the prostatic tissue in the vicinity of verumontanum 100. Because antenna 174 is formed from two distinct wire sections 142 and 144, each having a generally uniform pitch, antenna 174 may be more easily manufactured.

Antenna 174 emits electromagnetic energy which varies along its axis in a step-wise manner. In particular, the SAR emitted by antenna 174 step-wise increases towards bladder neck 11 at connector 146 interconnecting sections 142 and 144. The emission of electromagnetic energy by sections 142 and 144, individually, is generally uniform along each section's axial length because each section has a generally uniform pitch along its length. Alternatively, the spacing between windings 180 or windings 182 of sections 142 and 144, respectively, may be varied along each section's axial length so that each section itself emits an asymmetric amount of electromagnetic energy along each section's length. As can be appreciated, antenna 174 may be formed from a multitude of different wire sections, different pitches and different axial lengths. In addition, antenna 174 may alternatively be formed so as to generate a conventionally known standing wave pattern emitting a greater volume and intensity of electromagnetic energy at proximal end 115 of antenna 174 than at distal end 114 of antenna 174 to deliver a greater amount of energy to prostate tissue in the vicinity of bladder neck 11 than in the vicinity of verumontanum 100.

FIGS. 7–10 illustrate alternative embodiments of the present invention for delivering asymmetrical or unequal amounts of energy to prostatic tissue along a longitudinal axis of a catheter between bladder neck 11 and verumontanum 100. As discussed above, catheters 28 and 128 include antennas 74 and 174, respectively, that asymmetrically emit electromagnetic energy to prostatic tissue along an axis of the antenna and the catheter, preferably with a greater amount of energy being delivered to prostatic tissue in the vicinity of the bladder neck than in the vicinity of the verumontanum. The energy delivered to prostatic tissue along the axis of the catheter is generally a function of the amount of energy emitted by the antenna towards the prostatic tissue less any energy shielded or absorbed by the catheter before reaching the prostate tissue and less any energy and heat extracted from the tissue and carried away by the catheter. Thus, in lieu of the antenna emitting different amounts of energy along an axis of catheter 28, the embodiments illustrated in FIGS. 7–11 alternatively shield, block or absorb different amounts of emitted energy before the energy reaches the prostatic tissue or conductively extract different amounts of energy (heat) from surrounding prostatic tissue and along the axis of the respective catheters to vary the amount of energy delivered to prostatic tissue.

Figure 7:
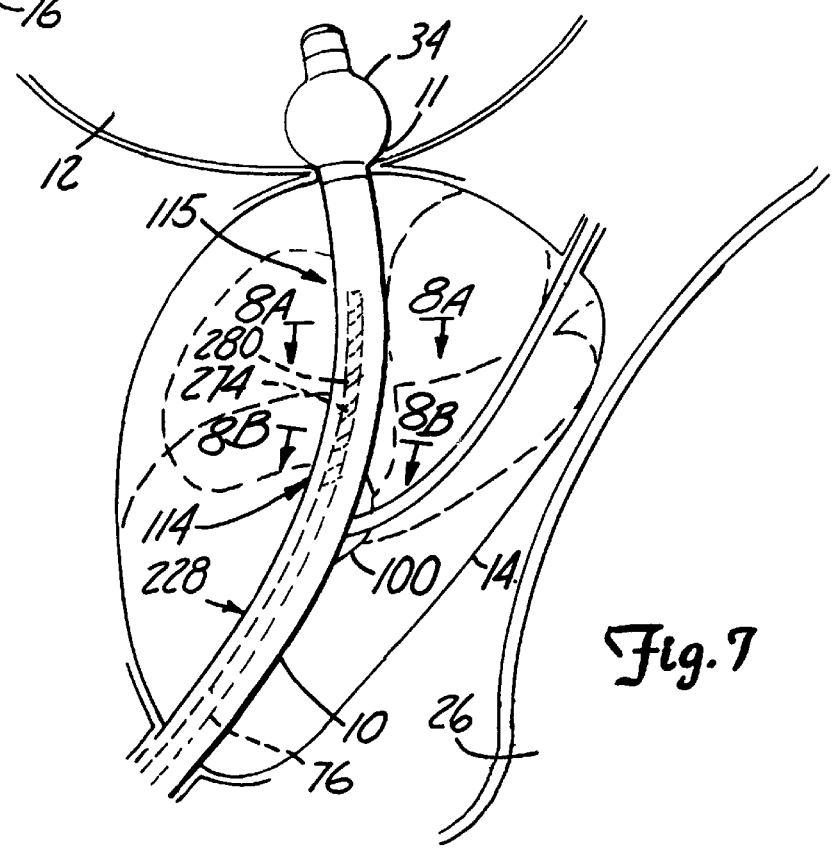
FIG. 7 is an enlarged vertical sectional view of a second alternate embodiment of the catheter of the present invention positioned within the prostate region.

FIG. 7 is an enlarged vertical sectional view of a proximal end of catheter 228, a second alternative embodiment of the present invention, inserted into a prostatic portion of urethra 10. Catheter 228 has all the attributes and features of catheters 28 shown in FIGS. 2–6 except that catheter 228 includes antenna 274, cooling fluid intake lumens 264A, 264B (shown in FIGS. 8A and 8B) and cooling fluid exhaust lumens 266A, 266B (shown in FIGS. 8A and 8B), in lieu of antenna 74, cooling fluid intake lumens 64A, 64B and cooling fluid exhaust lumens 66A, 66B of catheter 28. Antenna 274 is similar to antenna 74 except that antenna 274 includes windings 280 that have a uniform pitch or spacing along the axial length of antenna 274. As a result, antenna 274 emits a relatively uniform volume and SAR of electromagnetic energy to prostatic tissue along the axial length of antenna 274. However, cooling fluid intake lumens 264A, 264B and cooling fluid exhaust lumens 266A, 266A (shown in FIGS. 8A and 8B) are configured to asymmetrically absorb electromagnetic energy along the axial length of antenna 274 so that catheter 228 delivers a greater amount of electromagnetic energy to prostatic tissue proximate to bladder neck 11 than proximate to verumontanum 100.

Figure 8A:
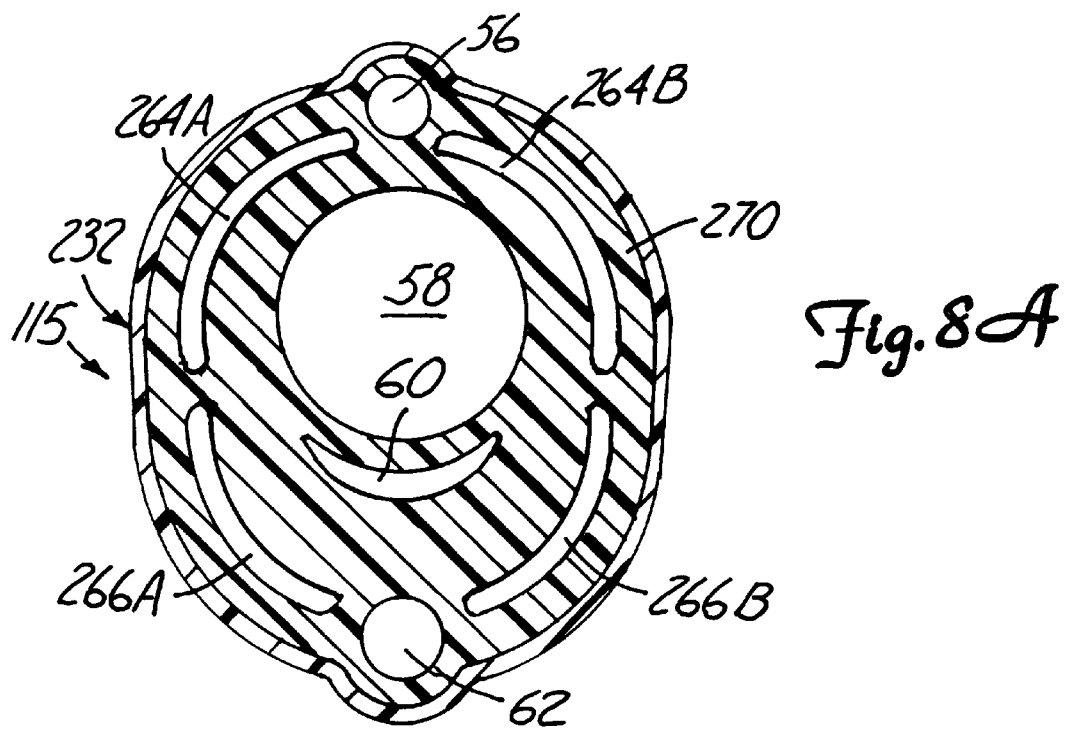
FIG. 8A is a cross-sectional view of the urethral catheter of FIG. 7 taken along line 8A—8A of FIG. 7.
Figure 8B:
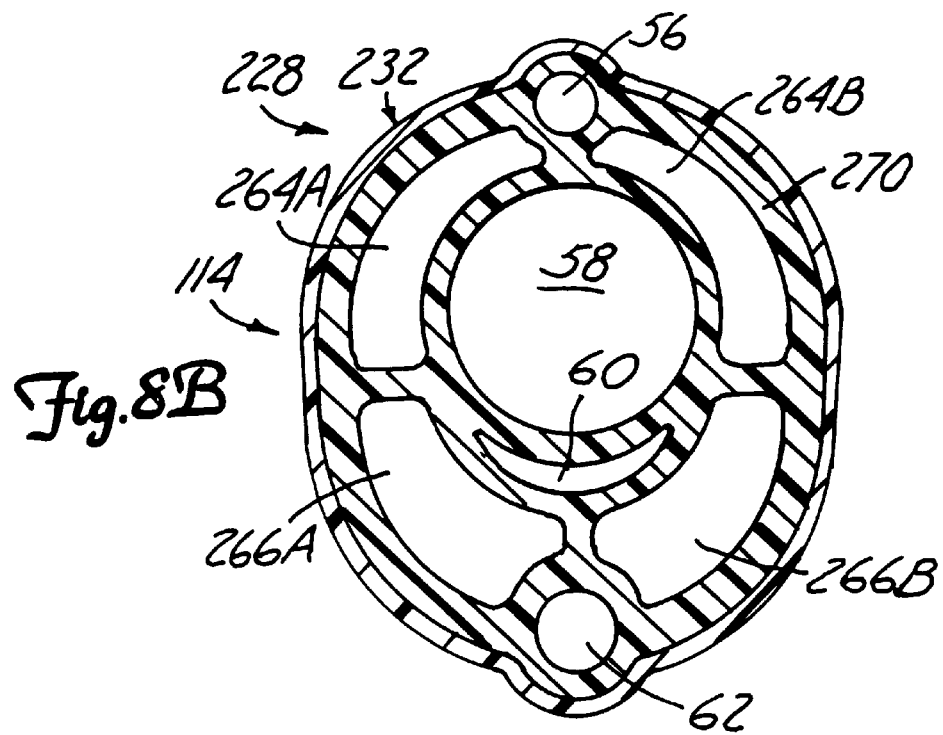
FIG. 8B is a cross-sectional view of the urethral catheter of FIG. 7 taken along line 8B—8B of FIG. 7.

FIGS. 8A and 8B are cross-sectional views of shaft 232 of catheter 228 taken along lines 8A—8A and 8B—8B respectively. FIGS. 8A and 8B illustrate the longitudinally varying cross-sectional dimensions of cooling fluid intake lumens 264A and 264B and cooling fluid exhaust lumens 266A and 266B as a way to variably absorb energy emitted by antenna 274 and thereby to vary the amount of energy delivered to prostatic tissue. As shown in FIGS. 8A and 8B, cooling fluid intake lumens 264A and 264B have a reduced cross-sectional area at a proximal-most end 115 of antenna 274 (shown in FIG. 7) as compared to a distal-most end 114 of antenna 274 (shown in FIG. 7). Similarly, cooling fluid exhaust lumens 266A and 266B have a reduced cross-sectional area at proximal-most end 115 of antenna 274 as compared to distal-most end 114 of antenna 274. In other words, cooling fluid lumens 264A, 264B, 266A and 266B have a larger cross-sectional area in the vicinity of catheter 228 corresponding to verumontanum 100 and a smaller cross-sectional area in the vicinity of catheter 228 corresponding to bladder neck 11. Preferably, the cross-sectional area of lumens 264A, 264B, 266A and 266B is gradually reduced from distal end 114 to proximal end 115 of antenna 274. Alternatively, the cross-sectional areas of lumens 264A, 264B, 266A and 266B may be step-wise reduced as desired. Because the cross-sectional areas of lumens 264A, 264B, 266A and 266B are varied along the axial length of catheter 228, the amount of energy absorbed by fluid circulating within lumens 264A, 264B, 266A and 266B is also varied. Accordingly, a greater amount of electromagnetic energy is delivered to prostatic tissue proximate to bladder neck 11 than proximate to verumontanum 100.

FIGS. 9A and 9B are cross-sectional views of shaft 332 of catheter 328, a third alternative embodiment of the present invention. Catheter 328 is similar to catheter 228 except that catheter 328 includes shaft 332 in lieu of shaft 32. For ease of illustration, those elements of catheter 328 that are the same as corresponding elements of catheter 228 are numbered similarly. Shaft 332 is similar to shaft 232 of catheter 228 except that shaft 332 includes cooling fluid intake lumens 364A, 364B, cooling fluid exhaust lumens 366A, 366B and wall 370. Cooling fluid intake lumens 364A, 364B and cooling fluid exhaust lumens 366A, 366B are essentially identical in dimension to cooling fluid intake lumens 64A, 64B and cooling fluid exhaust lumens 66A, 66B of FIGS. 3 and 4. Wall 370 of shaft 332 has a cross-sectional thickness which varies along the axial length of shaft 332 circumjacent to antenna 274 (shown in FIG. 7).

As shown by FIG. 9B, wall 370 encircling and circumjacent to cooling fluid intake lumens 364A and 364B and cooling fluid exhaust lumens 366A and 366B at the proximal-most end 115 of antenna 274 is thicker than wall 370 at the distal-most end 114 of antenna 274 (shown in FIG. 9B). The increased thickness of wall 370 at the proximal-most end 115 of antenna 274 decreases the amount of energy extracted from surrounding prostatic tissue by the cooling fluid circulating through lumens 364A, 364B, 366A and 366B to lower the conductive cooling coefficient of catheter 328 towards the proximal-most end 115 of antenna 274. As a result, the cooling fluid circulating through lumens 364A, 364B, 366A and 366B absorb a greater amount of energy in the vicinity of verumontanum 100 than in the vicinity of bladder neck 11. Thus, catheter 328 delivers a correspondingly greater amount of energy to prostatic tissue in the vicinity of bladder neck 11 than in the vicinity of verumontanum 100. The thickness of outer wall 370 of shaft 332 is preferably gradually decreased from the vicinity of bladder neck 11 towards the vicinity of verumontanum 100. Alternatively, the thickness of outer wall 370 may be step-wise decreased. Thus, because the thickness of wall 370 varies to vary thermal conductivity of wall 370, the amount of energy or heat conductively extracted from surrounding prostatic tissue by the circulating cooling fluid also varies along the axial length of shaft 332 between bladder neck 11 and verumontanum 100. As can be appreciated, the thermal conductivity or energy absorbing characteristics of wall 370 may be varied along the axial length of shaft 332 between bladder neck 11 and verumontanum 100 by various alternative shaft configurations. For example, in lieu of having a varying thickness along an axis of shaft 332, wall 370 may alternatively be formed from different materials or different blends of different materials having varying energy absorbing and thermal conducting characteristics so that catheter 328 delivers asymmetrical amounts of energy between bladder neck 11 and verumontanum 100 as desired. Furthermore, the thermal absorbing characteristics of catheter 328 may alternatively be varied along the axial length of shaft 332 by providing at least two distinct cooling fluid circulation lumens along distinct axial segments of shaft 332 and by circulating cooling fluids through each distinct lumen at different temperatures or flow rates.

Figure 10:
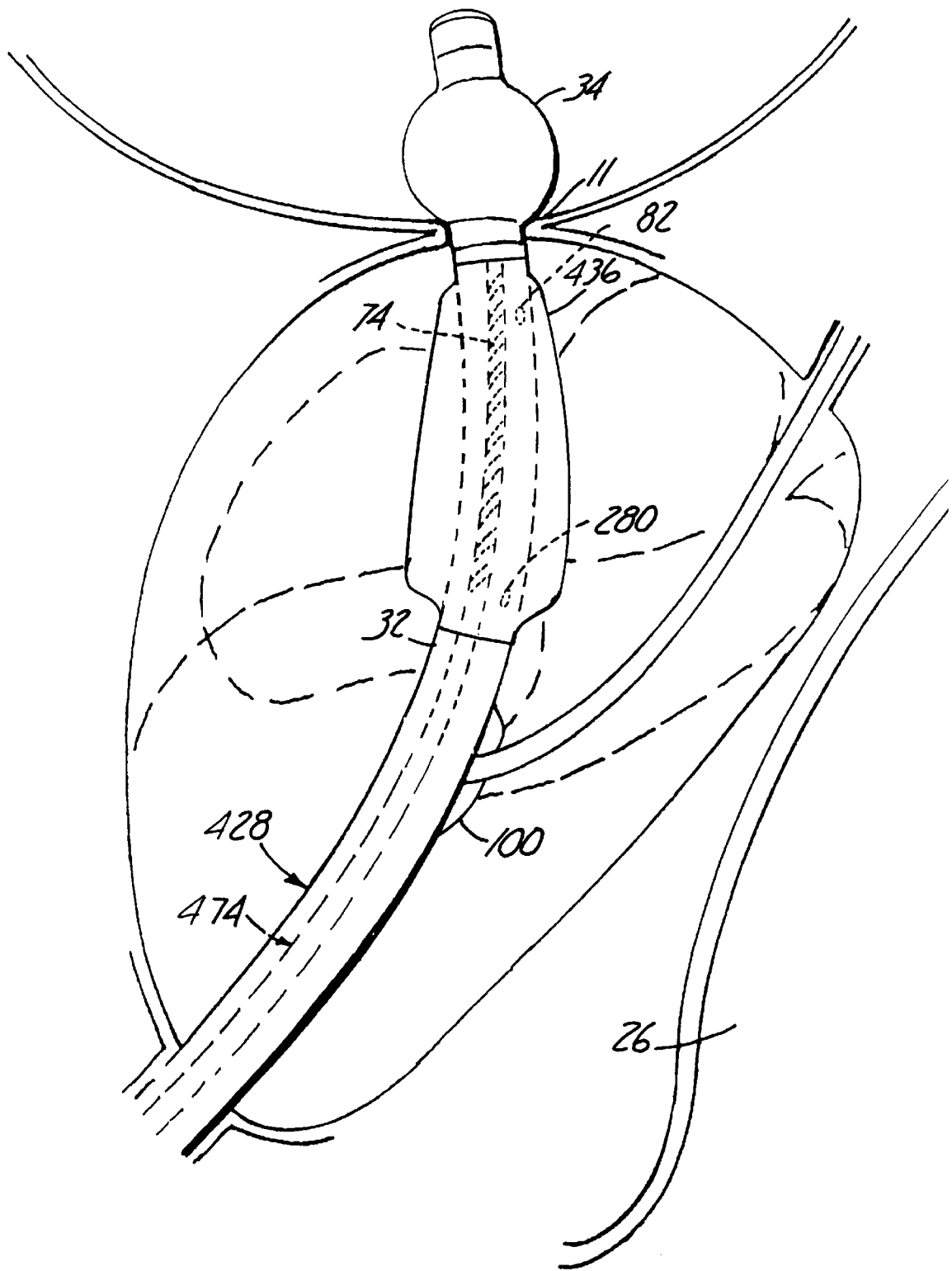
FIG. 10 is a vertical sectional view of a fourth alternate embodiment of the urethral catheter of the present invention positioned within the prostate region.

FIG. 10 is an enlarged vertical sectional view of prostate 14 with catheter 428, a fourth embodiment of the present invention. Catheter 428 has all the attributes and features of catheter 28 except that catheter 428 includes antenna 474 in lieu of antenna 74, and cooling balloon 436. Antenna 474 is similar to antenna 74 except that antenna 474 includes windings 480 which are uniformly spaced apart along the axis of antenna 474 to provide for uniform emission of electromagnetic radiation along the axis of antenna 374.

Cooling balloon 436 is an elongate inflatable balloon encircling shaft 32 and having a hollow cross-sectional area for being filled with a cooled fluid. Cooling balloon 436 extends along an axis of catheter 428 proximate to antenna 474. Opposing ends of balloon 436 are preferably secured on proximal end of shaft 32 with an adhesive. Balloon 436 is supplied with a cooled fluid from exhaust lumen 66B through hole 380 and exits from balloon 436 into exhaust lumen 66A through hole 382. Holes 480 and 482 are axially and laterally spaced apart to create a pressure differential between holes 480 and 482 causing a passive inflation of cooling balloon 436 and ensuring that adequate fluid circulation will occur through cooling balloon 436 as cooling fluid moves through cooling lumen 64A, 64B and 66A, 66B. Balloon 436 has a radially tapered inner and outer circumference which defines a relatively small cross-sectional area for cooled fluid adjacent to a proximal end 115 of antenna 474 proximate to bladder neck 11 and a relatively large cross-sectional area adjacent to a distal end 115 of antenna 474. As a result, microwave energy emitted from antenna 474 is absorbed in varying quantities along the length of balloon 436, with a greater amount of energy being absorbed adjacent to the distal end of antenna 374 than adjacent to the proximal end of antenna 474. With catheter 428 properly positioned in situ, catheter 428 delivers a greater amount of electromagnetic energy to prostatic tissue proximate to bladder neck 11 than to prostatic tissue proximate to verumontanum 100.

Figure 11:
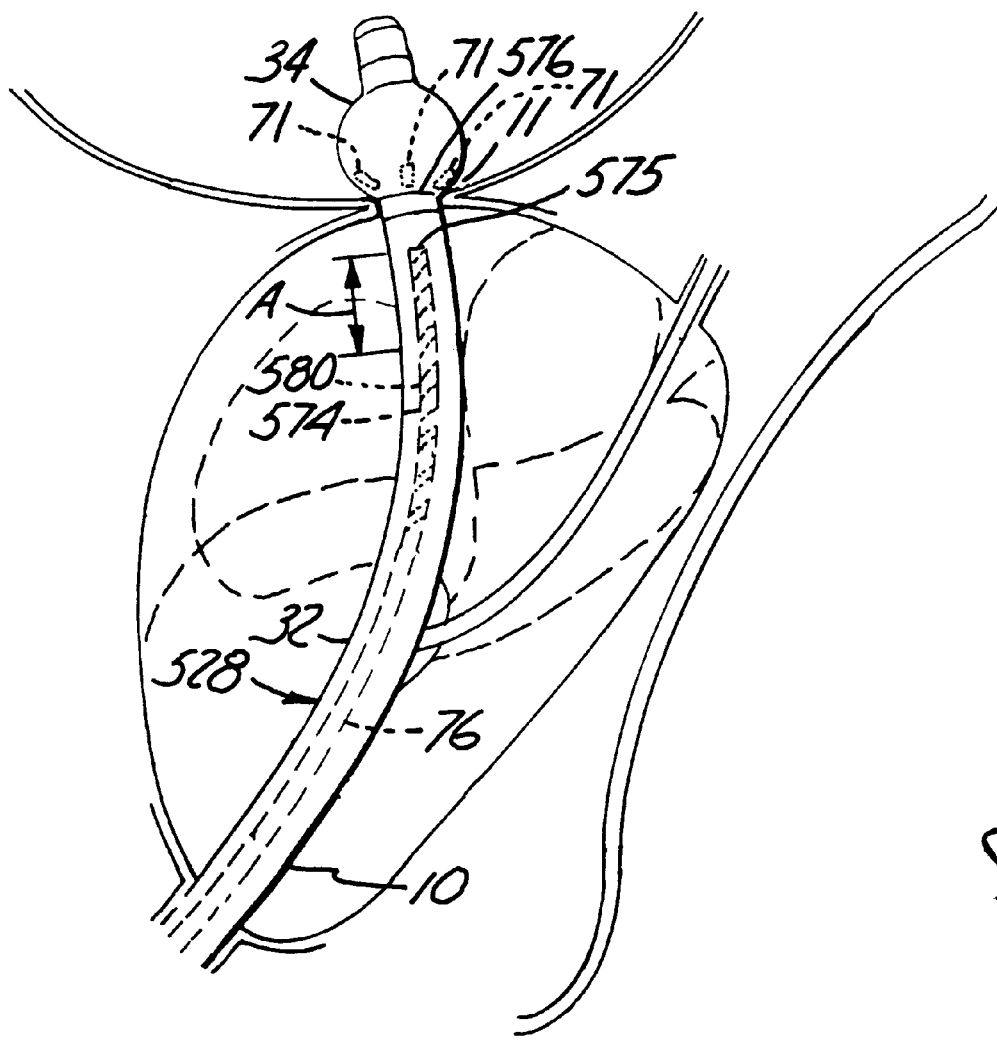
FIG. 11 is a vertical sectional view of a fifth alternate embodiment of the urethral catheter of the present invention positioned within the prostate region.

FIG. 11 is an enlarged vertical sectional view of prostate 14 with catheter 528, a fifth alternative embodiment of the present invention. Catheter 528 has all the features and attributes of catheter 28 except that catheter 528 includes antenna 574 in lieu of antenna 74. Antenna 574 is similar to antenna 74 except that antenna 574 includes windings 580 which helically encircle cable 76 and which are equally spaced from one another for uniformly emitting electromagnetic radiation along the length of antenna 574. In this alternative embodiment, antenna 574 is movable within lumen 58 of shaft 32 of catheter 528 so that proximal end 575 of antenna 574 may be selectively positioned relative to balloon 34 and bladder neck 11. Catheter 528 permits precise positioning of antenna 574 based upon temperature signals received by urethral/bladder thermometry unit 38 shown in FIG. 2A and from bladder thermometry sensors 71A–71C.

In a preferred embodiment, antenna 574 is positioned in lumen 58 with proximal end 575 located approximately 0.5 cm from base 576 of retention balloon 34. Catheter 528 is inserted into urethra 10 and advanced until retention balloon 34 lies within bladder 12. Retention balloon 34 is then inflated, preferably with air, and catheter 528 is withdrawn sufficient amount to anchor retention balloon 34 against bladder neck 11. So positioned, thermosensors 71A–71C are oriented to sense the temperature of tissue of bladder neck 11. Power is then applied to antenna 574 to emit electromagnetic energy into hyperplastic prostatic tissues adjacent to antenna 574. Cooling fluid is coincidentally circulated through cooling lumens 64A, 64B, 66A and 66B to selectively deliver sufficient electromagnetic energy to the hyperplastic tissues to generate necrosis-producing temperatures in those tissues, and to protect the urethral wall from thermal damage. To ensure that as much hyperplastic tissue as possible is safely necrosed in the region of bladder neck 11, thermosensors 71A–71C are monitored. In one preferred embodiment, bladder neck 11 is maintained at a temperature below about 45° C. throughout the treatment, with antenna 574 being repositioned as necessary relative to base 576 of retention balloon 34 to maintain this temperature. Repositioning is preferably controlled in increments of approximately 0.5 mm, until the desired bladder neck temperature is achieved. Power is continuously applied through treatment, the duration of which is between about 30 minutes to about one hour. By this operation, hyperplastic prostatic tissue proximate to bladder neck 11 can be safely necrosed without thermally damaging bladder neck 11.

It has been recently discovered that the prostatic tissues in the vicinity of the bladder neck have a greater vascularity as compared to other regions of the prostate. Consequently, for an equal distribution of energy along the length of an antenna oriented in the urethra adjacent to the transition zone of the prostate and the bladder neck, less temperature elevation of tissue occurs in the hyperplastic prostatic tissue near the bladder neck than would be desirable. To safely increase the volume of hyperplastic tissue necrosed near the bladder neck which contribute to urethral obstruction, and thereby improve therapy, the various embodiments of the present invention are capable of producing a variable distribution of energy along the length of the antenna, with the greatest amount of energy being delivered next to the portion of the antenna which, in use, lies adjacent to the bladder neck. By delivering additional energy to these tissues, sufficient heat can be generated to overcome the heat dissipating capability of these more vascularized tissues. As a result, with the aid of temperature sensing of bladder neck tissues and a selective longitudinal distribution of energy in the prostate, an additional volume of obstructive prostatic tissue adjacent to the bladder neck can be safely necrosed without harming bladder neck tissue—an accomplishment which, to date, has not been possible.

The present invention delivers additional energy to hyperplastic prostatic tissue near the bladder neck to safely necrose an additional volume of obstructive prostatic tissue without harming bladder neck tissue. The present invention includes four general embodiments and methods which safely deliver additional energy to hyperplastic prostatic tissue near the bladder neck. First, the amount of energy emitted by the antenna may be varied along the axial length of the antenna to emit a greater amount of electromagnetic energy near the bladder neck. Second, the amount of electromagnetic energy absorbed by the catheter may be varied along the axial length of the catheter, with a smaller amount of energy absorbed by the catheter near the bladder neck. Third, the amount of energy or heat conductively extracted from surrounding prostatic tissue may be varied along the length of the catheter, preferably with a smaller amount of energy being extracted from surrounding prostatic tissue near the bladder neck. Lastly, the energy emitting antenna may be selectively moved relative to the bladder neck based upon temperature sensing of bladder neck tissues to necrose an additional volume of obstructive prostatic tissue adjacent the bladder neck without harming the bladder neck tissue. Although each of these general methods and embodiments for necrosing an additional volume of obstructive prostatic tissue adjacent the bladder neck have been described independent of one another, the scope of the present invention also encompasses the selective combination of each of these distinct methods and structures to achieve a desired volume of prostatic tissue necrosis.

Although the present invention has been described with reference to preferred embodiments, workers skilled in the art will recognize that changes may be made in form and detail without departing from the spirit and scope of the invention.

What is claimed is:

1. A method of prostate treatment comprising:
   inserting into a prostatic portion of a urethra an energy emitting device, the energy emitting device having an energy delivering portion and being connectable to an energy source;
   delivering an energy distribution to the prostate from the energy delivering portion of the energy emitting device, an intensity of the energy distribution delivered to prostatic tissue being varied along an axial length of the energy delivering portion of the energy emitting device to treat a desired volume of the prostate; and wherein the step of inserting comprises locating an insertion end of the energy delivering portion of the energy emitting device adjacent to a bladder neck and wherein the step of delivering energy comprises heating the desired volume of prostatic tissue surrounding the energy delivering portion of the energy emitting device to a predetermined temperature for a sufficient time to necrose the desired volume of prostatic tissue, a temperature distribution within the desired volume, relative to the energy delivering portion of the energy emitting device, being approximately equal along the axial length of the energy delivering portion of the energy emitting device.

2. A method of prostate treatment comprising, inserting into a prostatic portion of a urethra an energy emitting device, the energy emitting device being connectable to an energy source;

delivering energy to the prostate from the energy emitting device, the intensity of energy delivered to prostatic tissue adjacent to a bladder being greater than the intensity of energy delivered to prostatic tissue distant from the bladder; and wherein the step of inserting comprises locating an insertion end of the energy emitting device adjacent to a bladder neck and wherein the step of delivering energy comprises heating the desired volume of prostatic tissue surrounding the energy emitting device to a predetermined temperature for a sufficient time to necrose the desired volume of prostatic tissue, a temperature distribution within the desired volume, relative to the energy emitting device, being approximately equal along an axial length of the energy emitting device.

3. A method of prostate treatment comprising:

inserting an energy emitting device into a prostatic portion of a urethra; and operating the energy emitting device to necrose a substantially constant depth of prostatic tissue in a specified radial direction along an axial length of the energy emitting device.

4. A method of treating a prostate comprising:

delivering a first intensity of energy to necrose a first region of the prostate adjacent to a bladder; and delivering a second intensity of energy to necrose a second region of the prostate distant from the bladder, the first intensity of energy being greater than the second intensity of energy.

* * * * *